(12) United States Patent  
Brahme et al.

(10) Patent No.: US 7,693,256 B2  
(45) Date of Patent: Apr. 6, 2010

(54) PHASE-CONTRAST X-RAY IMAGING

(75) Inventors: Anders Brahme, Danderyd (SE); Shu-Ang Zhou, Alvsjo (SE)

(73) Assignee: C-Rad Innovation AB, Uppsala (SE)

( * ) Notice: Subject to any disclaimer, the term of this patent is extended or adjusted under 35 U.S.C. 154(b) by 0 days.

(21) Appl. No.: 12/051,264

(22) Filed: Mar. 19, 2008

(65) Prior Publication Data

US 2009/0238334 A1   Sep. 24, 2009

(51) Int. Cl.
*A61B 6/02* (2006.01)
(52) U.S. Cl. .......................................... 378/41; 378/62
(58) Field of Classification Search ................... 378/41, 378/62
See application file for complete search history.

(56) References Cited

U.S. PATENT DOCUMENTS

| | | | |
|---|---|---|---|
| 4,737,972 A | 4/1988 | Schoolman | |
| 5,802,137 A | 9/1998 | Wilkins | |
| 2002/0041653 A1* | 4/2002 | Wilkins et al. | 378/98.9 |
| 2005/0053192 A1* | 3/2005 | Sukovic et al. | 378/41 |

| | | | |
|---|---|---|---|
| 2006/0039532 A1 | 2/2006 | Wu et al. | |

FOREIGN PATENT DOCUMENTS

| | | |
|---|---|---|
| EP | 0 799 600 A2 | 10/1997 |
| EP | 1 447 046 A1 | 8/2004 |
| GB | 2 401 953 A | 11/2004 |
| WO | WO 2007/100823 A2 | 9/2007 |

OTHER PUBLICATIONS

International Search Report, dated Jul. 14, 2009, and Written Opinion of the Iternational Searching Authority.

\* cited by examiner

*Primary Examiner*—Hoon Song
(74) *Attorney, Agent, or Firm*—Young & Thompson

(57) ABSTRACT

A stereoscopic phase-contrast X-ray imaging system (1) comprises a stereoscopic radiation head (20) having at least one X-ray source (30, 31) providing a first (32) and second (33) X-ray beam in stereoscopic configuration onto an object (110). At least one detector (40, 41) detects the beams (32, 33) having passed through the object (110) and generates detection data. This data is processed by a phase-contrast stereoscopic reconstruction processor (60) to generate two 2D phase-contrast images (80, 82) of the object (110) collectively forming a stereoscopic image pair or stereo image providing high resolution 3D representation of the object (110).

25 Claims, 8 Drawing Sheets

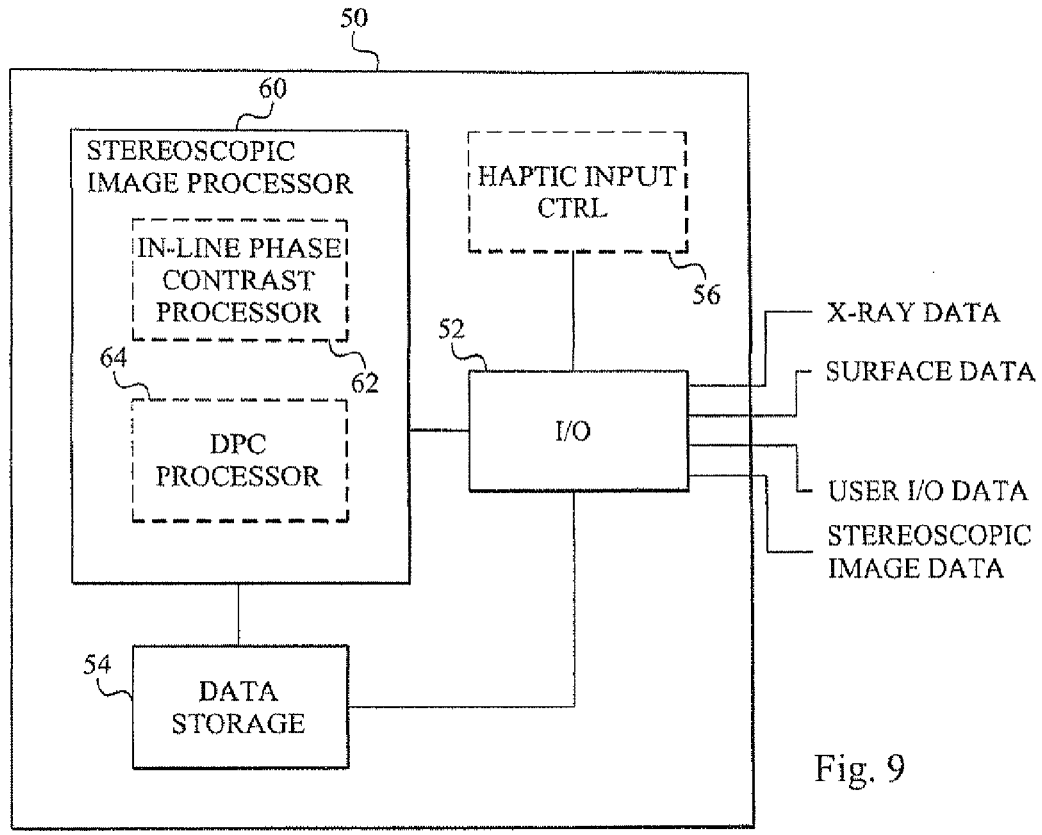
Fig. 9
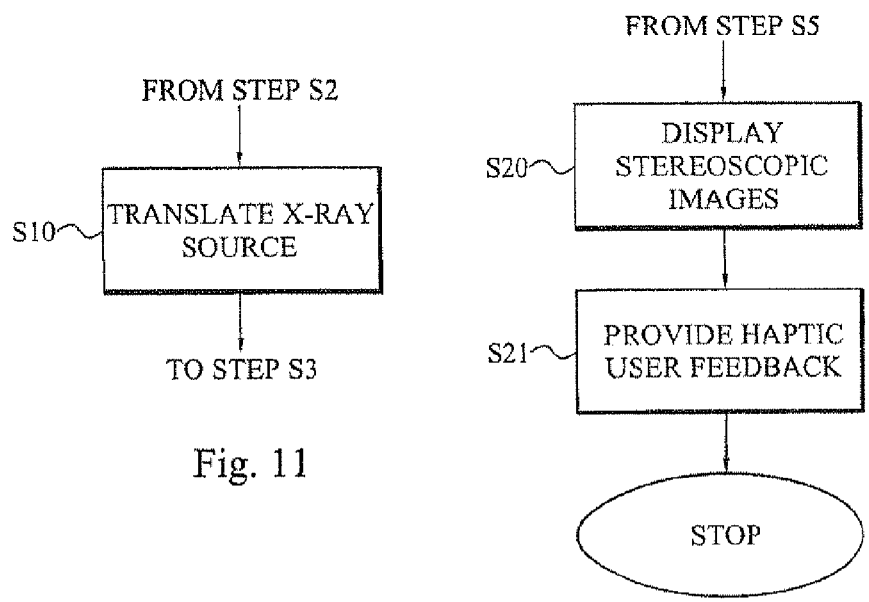
Fig. 11
Fig. 12

PHASE-CONTRAST X-RAY IMAGING

TECHNICAL FIELD

The present invention generally relates to X-ray imaging, and in particular to a diagnostic phase-contrast X-ray imaging system and method.

BACKGROUND

Diagnostic imaging is an important tool of medical and veterinary healthcare today. In particular, X-ray imaging is routinely employed for visualizing different (normal, affected or malignant) tissues in the human and animal body. Furthermore, diagnostic imaging is also employed for imaging other types of material than whole animal bodies, including in vitro tissue imaging and non-biological imaging. An example of the latter is security control imaging.

X-rays penetrate the investigated material and become absorbed mainly by photoelectric effect and Compton scattering due to the atoms in the material. The absorption amount of the X-ray depends on the attenuation coefficient of the given material, which in turn depends on its atomic weight and density. Traditional absorption or attenuation based X-ray imaging, thus, acquires a two-dimensional (2D) image of the X-ray intensity differences in the material. Such attenuation based X-ray imaging works rather well for several medical applications though has limitations in a relative low contrast, sharpness, resolution and image quality in soft tissue regions of medical interest.

Improvements have and are continuously developed in the field of X-ray imaging. The problem of low contrast was solved in the early 1970's by one of the most significant breakthroughs in diagnostic imaging, namely X-ray computed tomography. In X-ray CT, several hundreds of X-ray images are generally taken of a patient from different views 360° around the patient body. These multiple images are co-processed in order to provide a high contrast three-dimensional (3D) representation of a portion of the patient body.

In the very beginning of CT imaging, the X-ray gantry was static with a rotating object, though further developments was rapidly directed towards a static object by new X-ray CT generations with a rotating X-ray source and detector or only one or more rotating X-ray sources. Improvements relating to CT imaging have also taken place, among others, in the design of the radiation gantry, allowing ever faster rotations and image acquisitions from the different rotational views. Also the X-ray source and detector techniques for CT imaging have been improved highly since the first introduction of X-ray CT diagnosis.

CT imaging is though marred by several drawbacks, in particular due to the need for rotating the gantry around the object to be imaged. This, above, all limits the availability of X-ray sources that can be fit into a rotating gantry and can be designed to cope with the high rotational speeds of CT gantries (today about three revolutions per second). X-ray CT imaging also has too low contrast and geometrical and temporal resolution for several medical applications, including heart imaging and angiography.

SUMMARY

There is, thus, a need for a more efficient diagnostic imaging system allowing 3D imaging of objects, in particular live human and animal bodies, but without the limitations and drawbacks of traditional X-ray CT imaging.

It is a general object of the present invention to provide an improved X-ray imaging of high contrast, geometrical and temporal resolution.

It is a particular object of the invention to provide an X-ray imaging system and method capable of generating 3D representations of objects.

These and other objects are met by the invention as defined by the accompanying patent claims.

Briefly, the present invention involves a stereoscopic phase-contrast X-ray imaging system for generating structural representation data of an imaged object. The system comprises a stereoscopic X-ray radiation head, optionally supported by a stationary or movable gantry. The radiation head comprises at least one X-ray source arranged for directing a first X-ray beam and a second X-ray beam in stereoscopic configuration onto the object. This stereoscopic configuration implies that the two beams provide two different perspectives of the object, one representing what the left-eye and the other what the right-eye of a viewer is seeing.

At least one X-ray detector is arranged for detecting the first and second X-ray beams having passed through the object to generate a stereoscopic pair of detection data. This detection data is processed by a phase-contrast stereoscopic image reconstructing processor of the system. The processor generates, based on the detection data, two 2D phase-contrast images of a least a portion of the object. These two images collectively form a stereoscopic image pair or a so-called stereo image constituting a 3D image representation of at least a portion of the object allowing an efficient high-contrast, high-resolution visualization of the object portion.

In an optional embodiment, the system comprises two X-ray sources arranged in stereoscopic configuration in the radiation head. In such a case, the two X-ray sources are preferably activated at least almost simultaneously so that the application of the two X-ray beams substantially coincides in time. In such a case, it is possible to "freeze" internal structures of the object that are subject to internal motions, such as due to heart beating, breathing and peristaltic motions that otherwise would blur the images.

In another optional embodiment, the system comprises a surface imaging sub-system comprising a laser scanner arranged for scanning a laser fan beam onto at least a portion of the object surface. A photon detector detects the reflected laser beam from the object surface to generate surface detection data. The stereoscopic image reconstructing processor co-processes this surface detection data with the stereoscopic X-ray data for the purpose of generating a 3D image representation (stereo image) comprising, not only phase-contrast imaged structures, but also the skin surface that provides an accurate boundary envelope to the internal tissue structures to form a truly accurate 3D image volume of high quality that is well defined in space and time.

The present invention also relates to a stereoscopic phase-contrast X-ray imaging method generating a stereoscopic image pair of at least a portion of the object.

The invention offers the following advantages:

It provides high phase and attenuation contrast.
It provides high geometrical resolution and high temporal resolution.
It can be used in connection with varying X-ray sources, including large and cumbersome sources that are not implementable in connection with rapidly rotating gantries.
It results in low patient radiation dose.

Other advantages offered by the present invention will be appreciated upon reading of the below description of the embodiments of the invention.

SHORT DESCRIPTION OF THE DRAWINGS

The invention together with further objects and advantages thereof, may best be understood by making reference to the following description taken together with the accompanying drawings, in which:

FIG. 9 is a schematic block diagram of the image processing unit according to an embodiment of the present invention;

FIG. 11 is a flow diagram illustrating an additional step of the imaging method in FIG. 10;

FIG. 12 is a flow diagram illustrating additional steps of the imaging method in FIG. 10;

DETAILED DESCRIPTION

Figure 1:
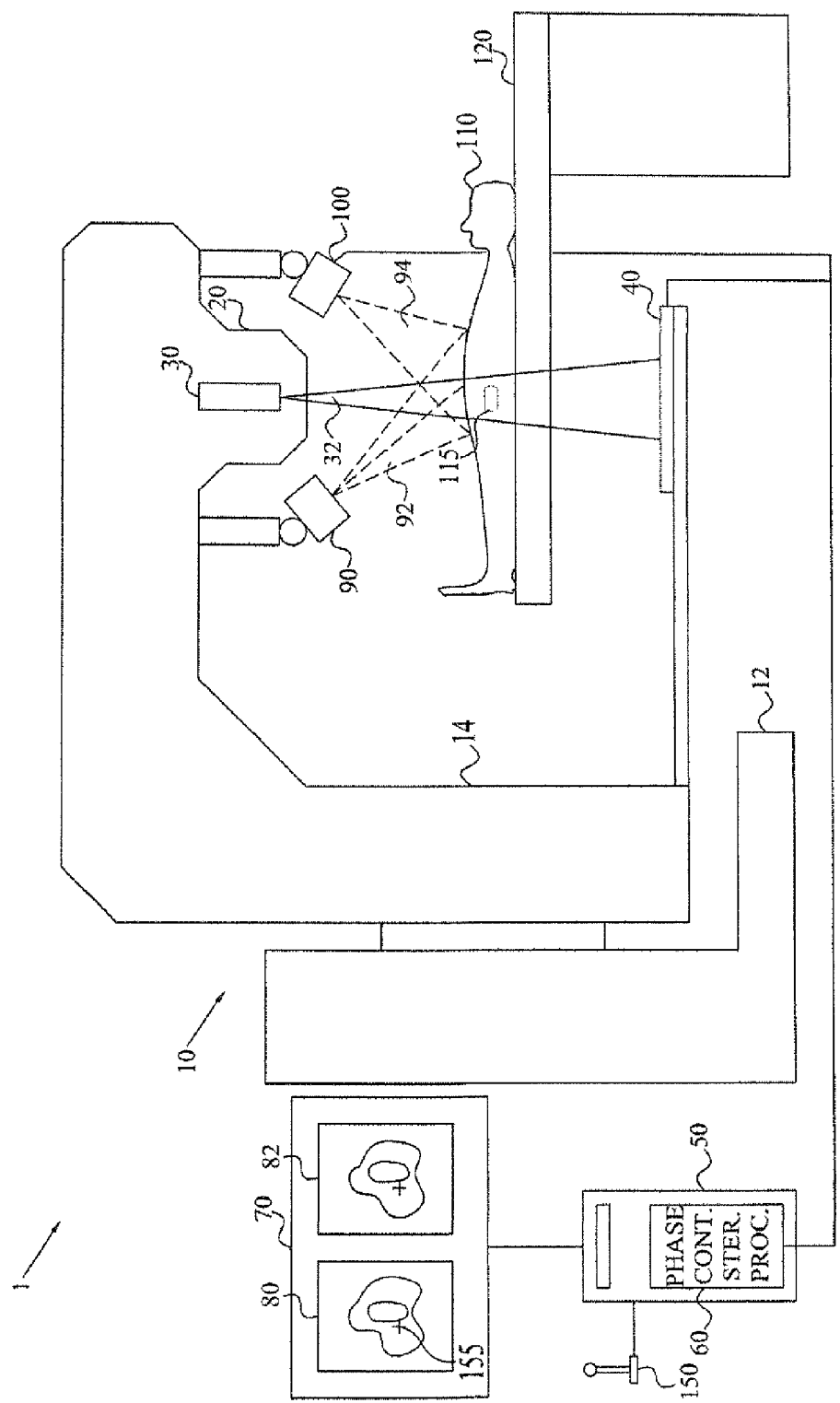
FIG. 1 is a schematic overview of a stereoscopic phase-contrast X-ray imaging system according to an embodiment of the present invention.

Throughout the drawings, the same reference characters will be used for corresponding or similar elements.

The present invention relates to imaging using phase-contrast X-ray techniques by providing a phase-contrast stereoscopic X-ray imaging system and method.

The present invention combines the advantages achievable from phase-contrast X-ray imaging with a stereoscopic set-up allowing three-dimensional (3D) perception and image creation at high-contrast and resolution using only a pair of stereopscopic 2D images.

In clear contrast to conventional attenuation-based X-ray imaging, phase-contrast imaging uses both the phase coefficient and the attenuation coefficient to image an object. Phase-contrast imaging therefore has the capability of resolving structures having similar attenuation coefficients but different phase coefficients as their surroundings. Furthermore, phase-contrast imaging is typically also an edge-enhancement imaging technique due refraction processes visualized using micro-focus X-ray tubes. This means that boundaries inside soft tissues and small structures can more easily be determined.

This high contrast and resolution of phase-contrast imaging and its ability to discriminate between even very small structures inside an object provide a high level of wealth of details. As a consequence, very complex structures with a lot of structural details are visible. However, such complex 2D images are generally very hard to interpret due to the high contrast and wealth of details. The present invention is based on these properties of phase-contrast imaging and takes advantage of its high contrast, high resolution nature to generate a 3D data set and allowing 3D display. This significantly facilitates interpretation of the imaged object and improves interpretation of the complex structures since they are separated from each other along the depth axis.

According to the invention, the 3D data set is obtained by utilizing a stereoscopic phase-contrast X-ray imaging system arranged for generating a stereoscopic pair of phase-contrast X-ray image data of an object. This image data set can be processed and displayed as a stereoscopic image pair or stereo image facilitating, by means of stereoscopic viewing tools, a true 3D representation of an object from two 2D phase-contrast images.

FIG. 1 is a schematic overview of an embodiment of a phase-contrast stereoscopic X-ray imaging system 1 according to the present invention. The system 1 comprises a radiation gantry 10 having or mechanically supporting a stereoscopic X-ray radiation head 20. The gantry 10 may optionally, as is illustrated in FIG. 1, comprise a static gantry part 12 movably (rotatably) supporting a movable (rotary) gantry part 14. In such a case, the radiation head 20 forms a part of or is attached to the movable gantry part 14. The radiation head 20 and the movable gantry part 14 can then be rotated around a rotation axis relative the static gantry part 12 to move an X-ray source between at least a first stereoscopic radiation position and a second stereoscopic radiation position, which is discussed further herein.

However, the imaging system 1 of the present invention is not limited to usage with a movable gantry 10. In clear contrast, a stationary gantry with a stationary stereoscopic X-ray radiation head 20 can also be used and is encompassed by the invention. Such a stationary or slowly rotating gantry can be advantageous in certain applications as they can be used in connection with X-ray sources that are not functionally implementable in (fast) rotating gantries.

The stereoscopic X-ray radiation head 20 comprises at least one X-ray source 30 arranged for directing a first X-ray beam 32 and a second X-ray beam in stereoscopic configuration onto an object 110. Stereoscopic configuration implies, in the present invention, that the two X-ray beams 32 from at least one X-ray source 30 are incident onto the object 110 at two different direction and perspective points. As a consequence, a left-eye and a right-eye image of the object 110, or at least a portion 115 thereof, can be obtained from these two X-ray beams 32.

The object 110 having a target volume or area 115 to be imaged is preferably an animal body, more preferably a mammalian body, such as a human body. In such a case, the imaged target volume 115 could be a portion of the animal or human body that is to be imaged for diagnostic purposes, such as detecting the presence of a tumor. However, the present invention is not limited to imaging animal objects but can actually also be used for imaging tissues and body parts, imaging cadaveric bodies or indeed imaging non-biological objects, for instance in connection with security control imaging.

The present invention has the advantage of being able to use vastly different X-ray sources in the phase-contrast X-ray imaging system, including traditionally cumbersome and large X-ray sources that are not implementable in a rotary gantry 10.

In a preferred embodiment, the X-ray source 30 is a high brightness X-ray source in order to facilitate detection and imaging of even minute structures in the imaged object. Recently, high-brightness (more than 100 times higher brightness than conventional rotating-anode X-ray source) polychromatic hard X-rays have been demonstrated based on the liquid-metal-jet anode electron impact technique [1, 2]. A compact quasi-monochromatic tunable inverse Compton scattering X-ray source of high-flux has also been demonstrated by the use of a free electron laser based on a linear electron accelerator technique [3, 4]. Also a compact synchrotron source has been developed achieving more then 1000 times higher brightness than conventional rotating-anode X-ray sources [5]. As a consequence, the X-ray source employed by the present invention can therefore advantageously be a liquid-metal-jet source, an inverse Compton X-ray source or a synchrotron source.

The X-ray source should preferably also be a microfocus or ultra-fine focus X-ray source, including microfocus X-ray tubes. Such X-ray sources that can be used by the present invention include Hamamatsu microfocus X-ray (MFX) source, Oxford Instruments Ultrabright microfocus X-ray source and Scandiflash X-ray tubes. Other possible X-ray sources include laser-driven X-ray sources.

The preferred fine focus of the X-ray source allows achieving high geometrical resolution of the detected stereoscopic image data. As a consequence, the present invention is able to achieve such a geometrical resolution down to the mm range and preferably down to the sub-mm range. It is actually possible by, among others, careful choice of the X-ray source to allow a resolution in the μm and even sub-μm range with the stereoscopic phase-contrast X-ray imaging system of the present invention.

In the figure, the X-ray source 30 has been illustrated in the form of an X-ray tube arranged in the radiation head 20. It is though anticipated by the present invention that part of the X-ray source and guiding system does not necessarily have to be implemented in the radiation head 20. In clear contrast, at least a portion of such a system could be arranged elsewhere in the gantry 10 or even be provided in an adjacent room or a more remote location. However, the X-ray source 30 provided in the radiation head 20 is regarded as the portion of such a system from which an X-ray beam 32 is directed onto an object 110 to be imaged, regardless of the implementation location of other system components.

At least one X-ray detector 40 is included in the imaging system 1 and is arranged for detecting the first and second X-ray beams 32 from the at least one X-ray source 30 after they have passed through the object 110.

The X-ray detector is preferably a digital detector generating digital detected data based on the detected X-ray beam 32 having passed through the object 110. Today there are several such digital X-ray detectors available on the market, which have a linear and ultra-fast response to the detected X-ray beam 32 [6, 7]. Such detectors have, as compared to traditionally X-ray screen-film system, wider dynamic range and higher contrast sensitivity, making them highly suitable for usage in the stereoscopic phase-contrast X-ray imaging system 1 of the present invention.

An example of such a linear, digital detector that can be used in the present invention is a gaseous single photon counter X-ray detector [8], which has been shown to be useful in 2D X-ray imaging. Another preferred detector embodiment that can be used in the present invention is a 2D gas electron multiplier (GEM) X-ray detector [9-11].

The detector 40 is connected to a phase-contrast stereoscopic image reconstructing processor 60. This processor 60 may be housed in a dedicated computer or other processing terminal 50 present in the radiation room or provided elsewhere. The reconstructing processor 60 processes the stereoscopic pair of detected data from the at least one detector 40 and generates a 3D representation of at least a portion of the object 110 in the form of two 2D phase-contrast images 80, 82 of a least a portion of the object 110. These two images 80, 82 collectively forming a stereoscopic image pair implying that 3D data can be obtained therefrom or a 3D presentation of the image data is possible by displaying the images 80, 82 in a stereoscopic view on a display screen 70, optionally requiring further stereoscope tools.

The processor 60 is preferably arranged for processing the stereoscopic pair of detected data to generate two binocular stereoscopic phase-contrast images 80, 82. It is well known that a third dimension, i.e. the relative depth of an object, can be inferred from a variety of visual cues present in the retinal images, aside from usual 2D images of on object. One such cue is binocular disparity, defined as the difference between the locations (relative the corresponding foveae) of the two retinal projections of a given point in space. The brain uses this disparity to achieve stereoscopic depth perception from a pair of binocular stereoscopic images 80, 82.

The projection of 3D anatomical information onto a 2D image in traditional phase-contrast X-ray imaging will obscure subtle difference in X-ray transmission implying that the subtle difference in subject attenuation-contrast as well as phase-contrast may not be visable. In particular, the large amount of extra information in a projected phase-contrast image will make it very difficult to interpret a single projected image of a thick complex object. This difficulty is eliminated by using the stereoscopic imaging of the present invention, allowing superimposed structures to be spatially separated along the depth axis, reducing the confounding effects of overlap or so-called summation artifacts.

As a consequence, the present invention is able to achieve 3D representations of at least a portion 115 of an imaged object at a high accuracy and resolution using only a pair of 2D images taken by a stereoscopic phase-contrast X-ray imaging system 1.

FIG. 1 illustrates the main and preferred system components of the stereoscopic phase-contrast X-ray imaging system 1 of the present invention. The invention, however, anticipates that further system units and components traditionally employed in connection with X-ray imaging, such an X-ray fluence detector, etc., can also be used and arranged adjacent to or connected to the gantry 10.

The invention provides significant advantages as compared to traditional X-ray CT systems and new developed phase-contrast X-ray CT systems [12]. Firstly, CT imaging is based on taking several hundreds of images of the object from different views 360° around the object. This requires the usage of a rotatable gantry and rotatable X-ray source. The rotation requirement limits the available X-ray sources that can be used, whereas the present invention that is implementable using stationary gantry and stationary X-ray sources can fully take advantage of the newly developed high contrast X-ray sources that cannot be used in connection with or are not adapted for any rotation. Secondly, generally about 300-400 different images are taken during the rotations, implying that the object has to be irradiated 300-400 times during a typical CT session. However, even though the delivered dose per such irradiation time may be lower than one of the two irradiations of the present invention, the total accumulated dose per imaging session is significantly lower for the two beam applications of the present invention as compared to the several hundreds beam applications of prior art CT imaging.

Figure 2:
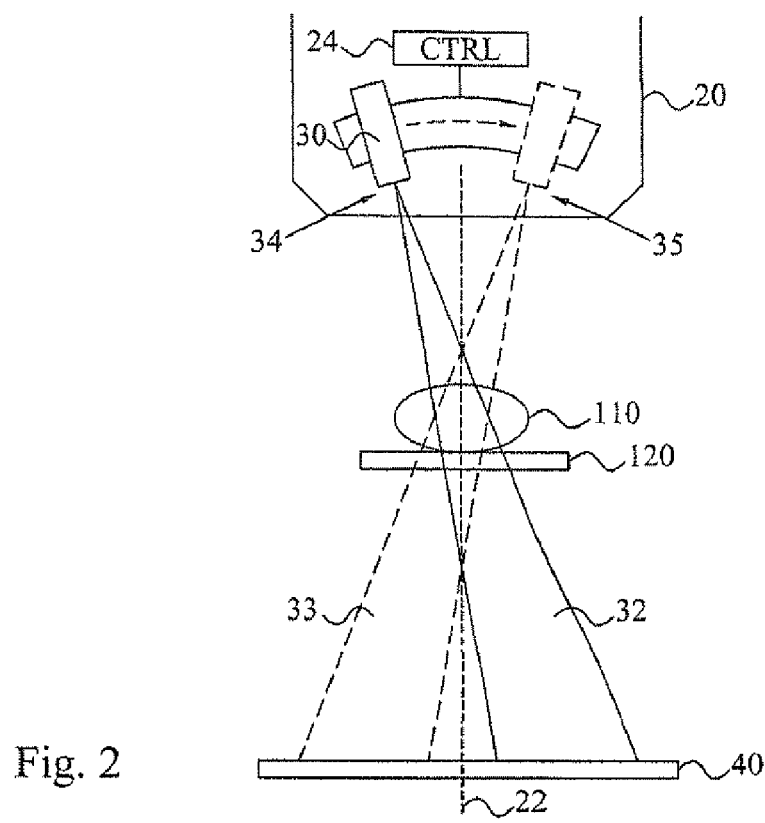
FIG. 2 illustrates in principle the stereoscopic phase-contrast X-ray imaging setup of an embodiment of the imaging system.

FIG. 2 illustrates in principle the stereoscopic phase-contrast X-ray imaging setup of a first embodiment of the imaging system. In this case, the stereoscopic radiation head 20 comprises a single X-ray source 30, such as a microfocus X-ray tube. The radiation head 20 also comprises a source translator 24 arranged for moving the X-ray source 30 from a first stereoscopic radiating position 34 to a second stereoscopic radiating position 35 in the radiation head 20. The translator 24 could, for instance, include a motor and control unit that controls the operation of the motor. The motor then provides the power for moving the source 30 between the radiating positions 34, 35 such as using a rail system in the head 20. In such a case, the X-ray source 30 directs the first X-ray beam 32 onto the object 110 at the first stereoscopic position 34 and directs the second beam 33 onto the object 110 at the second position 35. The at least one detector 40 is arranged on the opposite side of the radiation head 20 relative the object 110 on the couch 120 and detects the two radiation beams 32, 33 having passed through the object 110.

The two stereoscopic radiating positions 34, 35 are positioned to the left-hand side and the right-hand side of a central axis 22 of the imaging system. The movement or translation of the X-ray source 30 preferably proceeds in a direction parallel to the image plane from the left (right) to the right (left) of the central axis 22.

Figure 3:
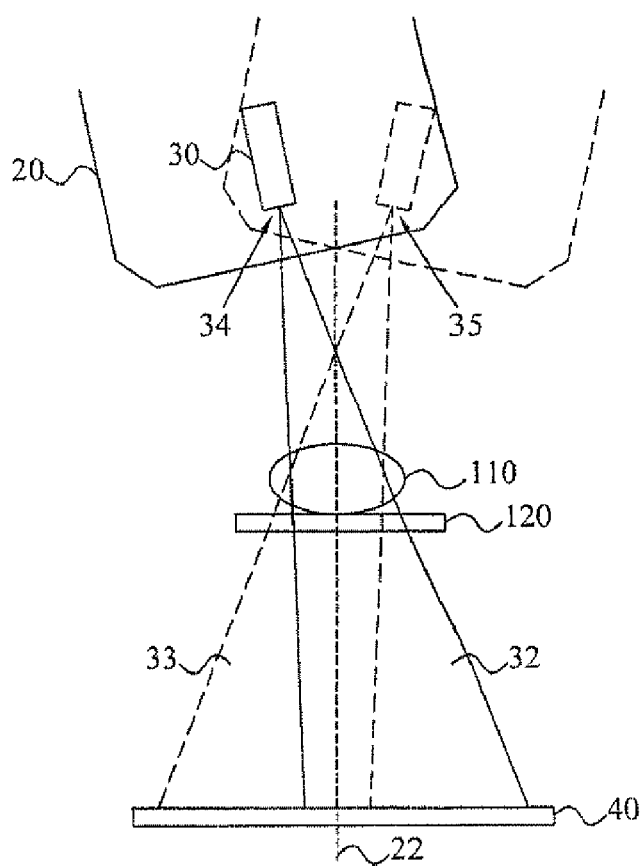
FIG. 3 illustrates in principle the stereoscopic phase-contrast X-ray imaging setup of another embodiment of the imaging system.

FIG. 3 illustrates an alternative embodiment of providing two stereoscopic radiating positions 34, 35 using a single X-ray source 30 in the radiation head 20. In this embodiment, the X-ray source 30 is preferably fixedly mounted in the radiation head 20. In clear contrast, the radiation head 20 is movable, e.g. rotatable, relative a static gantry part and relative the object 110 on the subject couch 120. In such a case, the radiation head 20 can be moved at least between a first position in which the X-ray source 30 is in the first stereoscopic radiating position 34 directing a first X-ray beam 32 onto the object 110 and a second position. In this second position, the X-ray source 30 has been moved through the rotational movement of the radiation head 20 or a movable gantry part to the second stereoscopic radiating position 35 directing a second X-ray beam 33 onto the object 110.

In the two embodiments disclosed in FIGS. 2 and 3 and discussed above, there is a period of time between directing the first X-ray beam 32 and the second X-ray beam 33 from the two stereoscopic positions 34, 35. This time period corresponds to the time required by the source translator 24 to move the X-ray source between the two positions 34, 35 or the time need for rotating the radiation head 20 (movable gantry part) to move the X-ray source 30 between the stereoscopic positions 34, 35.

Generally such a movement can be effected in the second range and even sub-second range.

Even though, such a fast movement may be sufficient for most diagnostic applications, there are situations where a second or sub-second time period between the two imaging occasions is too long. For instance, the heart with as many as 1-3 beats per second may be hard to freeze even with the fasted achievable source translator or gantry rotating equipment. There are also other portions of an animal body that are subject to internal movements, such as due to heart beats, breathing and peristaltic motions. In such a case, these internal motions may blur the images in particular if an internal organ or tissue to be imaged will move during the time period from applying and detecting the first X-ray beam to applying and detecting the second X-ray beam. This is a major problem in the X-ray CT systems of today.

The present invention can solve such problems and discloses embodiments achieving very high time resolutions allowing "freezing" of tissue and organs subject to internal movements.

Figure 4:
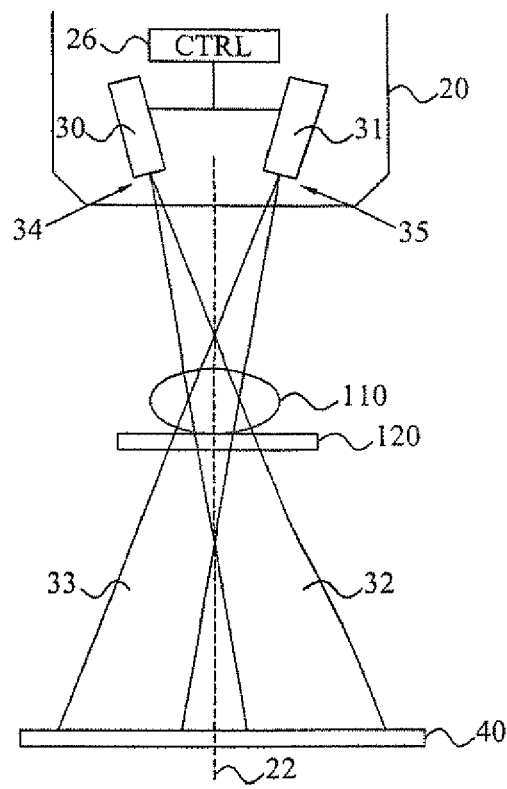
FIG. 4 illustrates in principle the stereoscopic phase-contrast X-ray imaging setup of a further embodiment of the imaging system.

FIG. 4 illustrates one such embodiment of the stereoscopic imaging system of the invention. In this case, the radiation head 20 comprises two X-ray sources 30, 31. A first X-ray source 30 is placed in the first stereoscopic radiating position 34 and is arranged for directing the first X-ray beam 32 onto the object 110. A corresponding second X-ray source 31 directs the second X-ray beam 33 onto the object 110 from the second stereoscopic radiating position 35.

The radiation head 20 may optionally include a source controller 26 connected to the two X-ray sources 30, 31. The controller 26 is preferably implemented to control the timing of irradiating the object 110 with the respective sources 30, 31. This controlled irradiation is preferably effected so that the application of the first X-ray beam 32 of the first source 30 coincides in time with application of the second X-ray beam 33 by the second source 31.

The radiation system can comprises a single detector 40 as illustrated in the figure. The detector 40 is then arranged for detecting both the X-ray beams 32, 33 having passed through the object 110 and originating from the two sources 30, 31.

This embodiment of the stereoscopic phase-contrast imaging provides the two stereoscopic image data without any significant time period between two imaging occasions. As a consequence, high time resolution is achievable allowing imaging of moving structures in an object which otherwise would not be well captured without motion blurring. This means that it is possible to achieve a time resolution dictated almost solely based on the beam pulse duration of the two X-ray beams 32, 33. Depending on the actual choice of X-ray sources 30, 31, this pulse duration could be in the order of 10-100 ms, though X-ray sources with much shorter pulse duration are available and can be used by the invention to achieve a time resolution in the range of µs, preferably a pulse duration of no more than 100 ns and more preferably no more than 50 ns. An example of such a fast X-ray source is the Scandiflash X-ray tube, which potentially can be used for ultra-fast imaging possibly down to tens of nano-seconds.

In the embodiment depicted in FIG. 4, the single detector 40 was employed for collecting the X-ray radiation of both beams 32, 33. This requires a detector area of adequate size in order to capture both radiation beams 32, 33 from the two stereoscopic radiating positions 34, 35.

Figure 5:
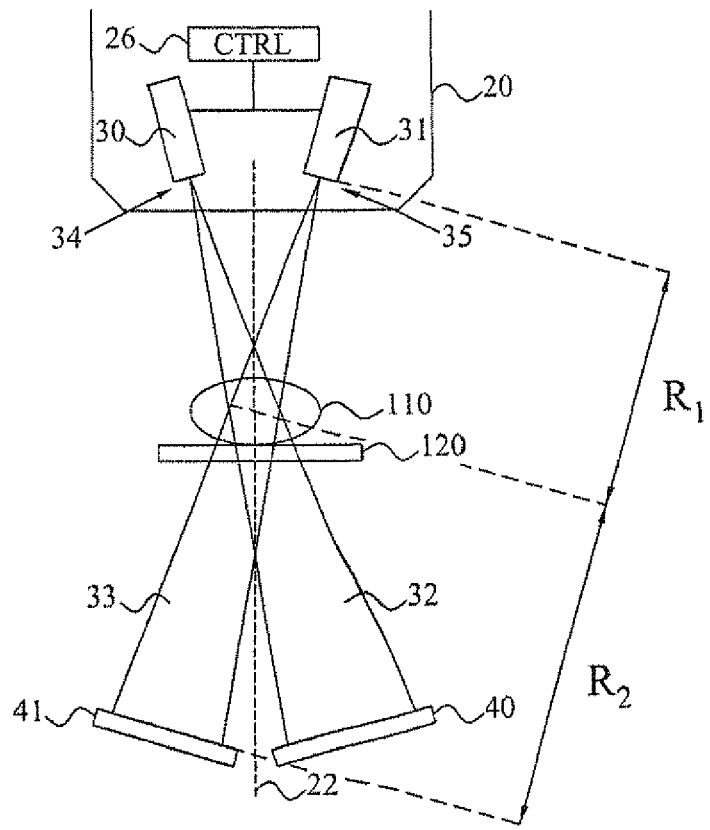
FIG. 5 illustrates in principle the stereoscopic phase-contrast X-ray imaging setup of yet another embodiment of the imaging system.

FIG. 5 illustrates an alternative embodiment using not only two X-ray sources 30, 31 but also two X-ray detectors 40, 41. A first detector 40 is then arranged for detecting the first X-ray beam 32 having passed through the object 110 and generating first detected data, preferably first digital detected data, based on the detected beam 32. A second X-ray detector 41 is likewise arranged for generating second (digital) detect data based on the detected second X-ray beam 33 from the second X-ray source 31. The first and second detected data collectively constitute the stereoscopic pair of detected data that is processed by the phase-contrast stereoscopic image reconstructing processor to obtain the 2D stereoscopic image pair and 3D data set of the invention. The two detectors 40, 41 are preferably of a same detector type arranged in the stereoscopic imaging system.

The figure also illustrates two distances: $R_1$ that is the distance between X-ray source 30, 31 and the object 110 and $R_2$ reflecting the distance between the object 110 and detector 40, 41. In a preferred embodiment the source-to-object distance $R_1$ is from about 20 cm to about 3 m, more preferably from about 0.5 m to about 1 m. In a typical embodiment the corresponding object-to-detector distance $R_2$ could be from about 10 cm to about 1 m, more preferably from about 0.25 m to about 1 m.

Figure 6:
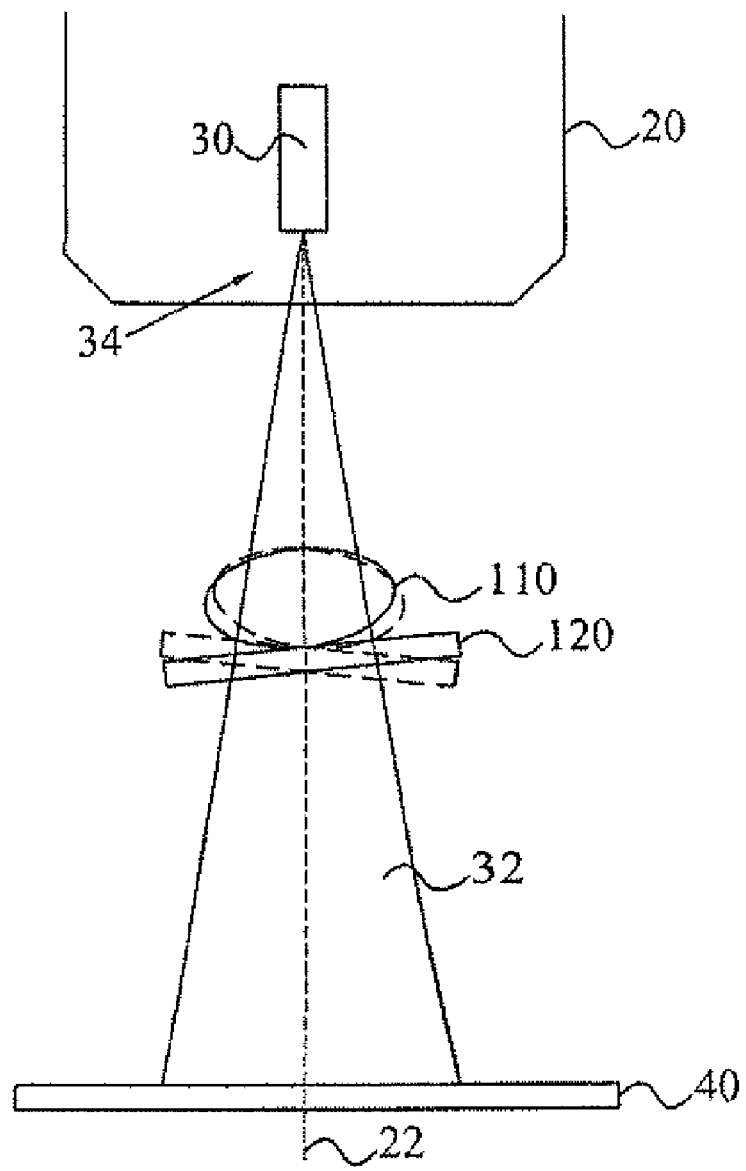
FIG. 6 illustrates in principle the stereoscopic phase-contrast X-ray imaging setup of still another embodiment of the imaging system.

FIG. 6 illustrates an alternative embodiment of obtaining stereoscopic phase-contrast X-ray images with a system of the present invention. In this embodiment the radiation head 20 is typically static and comprises a single, preferably static, X-ray source 30. In order to obtain two stereoscopic views of the object 110, the object couch 120 is moved (rotated) between a first position at which the X-ray source directs the first X-ray beam 32 and a second position at which the source 30 anew directs a beam onto the object 110. The patient couch 120 is then connected to a couch controller (not illustrated) comprising a motor and control unit for effecting the movement (rotation) of the couch 120 and the object 110 positioned thereon between the two imaging positions. Due to this couch rotation, the X-ray source 30 will see two stereoscopic views of the object 110 and thereby the at least one detector 40 generates a stereoscopic pair of detection data based on the first and second detected X-ray beam 32.

The teachings of the above described and in FIGS. 2-6 presented embodiments can be combined. For instance, two detectors can be used also in those embodiments illustrated in FIGS. 2-4 and 6. A rotatable couch can be used in connection with the embodiments of FIGS. 2-5 and a movable gantry portion can be used also in those embodiments depicted in FIGS. 1 and 3-6.

In the following different preferred phase-contrast X-ray imaging techniques and algorithms that can be used by the imaging system of the present invention, including the phase-contrast stereoscopic image reconstructing processor, are presented.

Differential Phase-contrast X-ray Imaging

Figure 7:
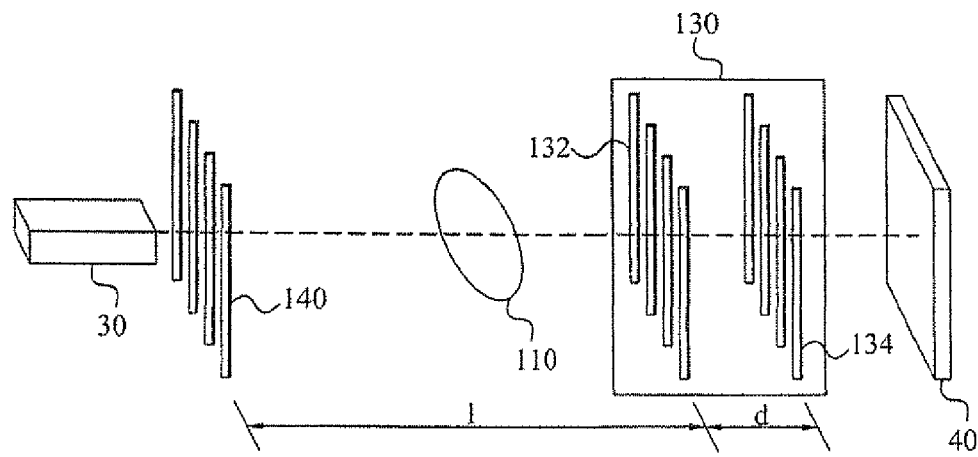
FIG. 7 illustrates the usage of an X-ray interferometer in the stereoscopic phase-contrast X-ray imaging system.

Differential phase-contrast (DPC) imaging is a recently introduced imaging technique capable of retrieving quantitative phase-contrast images with polychromatic X-ray sources of low brilliance FIG. 7 illustrates a typical set-up of a DPC system. The DPC solution is based on the usage of a number of gratings introduced in the beam path between the X-ray source 30 and the X-ray detector 40. These gratings preferably comprises a source grating 140, a phase grating 132 and an analyzer absorption grating 134 with their respective grating periods $p_0$ (source), $p_1$ (phase) and $p_2$ (absorption).

The source grating 140, typically realized as an absorbing mask with transmitting slits, placed close to the X-ray source 30, creates an array of individually coherent, but mutually incoherent sources. The ratio of the width of each line source to the period $p_0$ should be small enough to provide sufficient spatial coherence for the DPC image formation process. As the source mask 140 can contain a large number of individual apertures, each creating a sufficiently coherent virtual line source, conventional polychromatic X-ray sources 140 with sizes of more than a square millimetre can be used. In order to ensure that each line source produced by the source grating 140 contributes constructively to the image-formation process, the geometry of the set-up preferably satisfy the condition: $p_0 = p_2 l/d$, where l is the distance between the source grating 140 and the phase grating 132, and d is the distance between the phase grating 132 and the analyzer grating 134 [26].

A key part of the DPC system is a co-called Talbot interferometer 130 positioned between the object 110 and the detector 40. This Talbot interferometer 130 comprises the above-mentioned phase grating 132 facing the object 110 and the analyzer absorption grating 134 facing the X-ray detector 40, i.e. being arranged between the phase grating 132 and the detector 40. These two gratings 132, 134 act as an array of collimating slits that have a transmission depending strongly on the relative position of the two gratings 132, 134 and the angle of incidence. When the phase grating 132 is illuminated by coherent X-rays, periodic patterns (self-images) are generated at specific distances from the grating, which is known as the Talbot effect. If an object 110 is placed in front of the grating 132, it deforms the self-images, depending on the differential phase shift caused by the sample object 110. In the Talbot interferometer 130, the deformation is depicted in an area detector 40 as a moiré pattern, which is formed by the analyzer grating 134 placed on a self-image. The differential phase shift by the object 110 can be quantitatively retrieved by a fringe scanning technique, which is performed by moving one of the gratings in the direction of its period. Phase tomography may also be obtained by repeating the measurement at plural angular positions of the object rotation.

In this approach, any local phase gradient in the object 110 causes a local change in intensity recorded by the detector 40. For a weakly absorbing object 110, the detected intensity is a direct measure of the local phase gradient of the object 110 in this approach. The total phase shift of the object 110 can thus be retrieved by a simple integration. A higher precision of the measurement can be achieved by splitting a single exposure into a set of images taken for different positions of the analyzer grating 134. Thus, this approach allows the separation of the DPC signal from other contributions, such as non-negligible absorption in the object 110. Because the DPC image formation is not intrinsically coupled to the absorption of X-rays in the tissue medium of the object 110, radiation dose may potentially be reduced by using higher energy X-rays.

The DPC method has the advantage of using conventional polychromatic X-ray sources and X-ray detectors of moderate spatial resolution. Furthermore, high mechanical stability of the gantry is not required to perform DPC-based stereoscopic phase-contrast X-ray imaging.

In-line Phase-contrast X-ray Imaging

Figure 8:
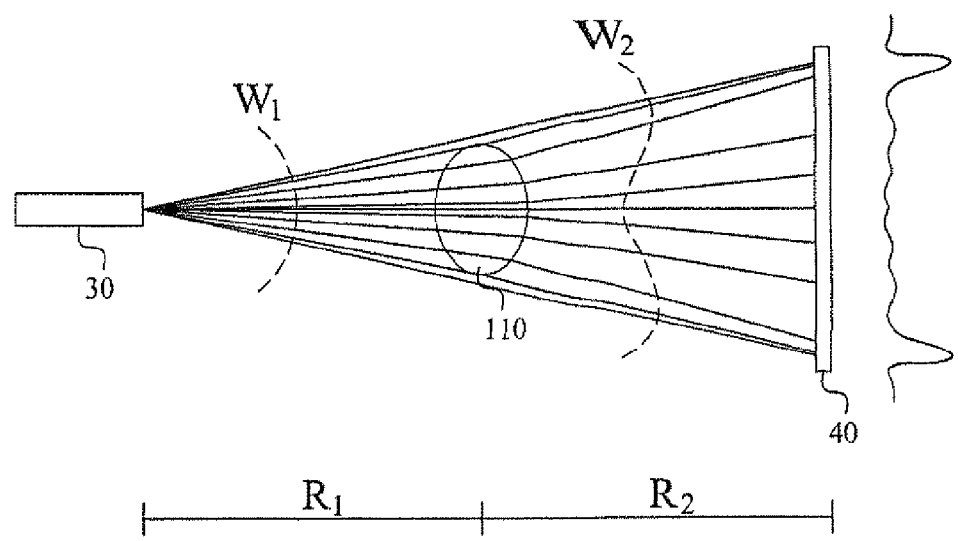
FIG. 8 illustrates the principles of stereoscopic in-line phase-contrast X-ray imaging.

The in-line phase-contrast imaging method, sometimes also called propagation-based imaging, the refraction enhanced imaging, or the in-line holography, exploits the Fresnel diffraction and dubbed phase-contrast imaging method. This technique is schematically illustrated in FIG. 8. With this method, X-rays transmitted through the sample object 110 at various angles will propagate over the distance between the object 110 and the detector 40. Variations in thickness and X-ray refractive index of the object lead to a change in the shape of an X-ray wave front $W_2$ on passing through the object 110 as compared to the X-ray wave front $W_1$ incident on the object 110.

When the detector 40 is located directly behind the object 110, a conventional absorption image is obtained, while at greater distances from the object 110, a phase-contrast image will be formed. The visual appearance of phase contrast enhancement in the final image is edge enhancement at interfaces between components with differing X-ray refractive indices. Since there is also a change of X-ray attenuation across these interfaces, the effect of the phase contrast is to provide a variable enhancement of the conventional attenuation image.

With this imaging modality, it is possible to use polychromatic X-ray sources 30. In order to achieve phase-contrast imaging, the X-ray source 30 should however provide a sufficient degree of spatial or lateral coherence, which can be characterized by the spatial (lateral) coherence width $L_{coh}$ of the source 30:

$$L_{coh} = \frac{\lambda R_1}{s}$$

where λ the wavelength of the X-ray beam, $R_1$ is the distance between the source 30 and the object 110, and s is the focal spot size of the X-ray source 30. It can be noticed here that the spatial coherence width $L_{coh}$ decreases with increasing X-ray photon energy. This implies that better edge-enhancing efficiency can be achieved by lower photon energy, for a given geometric configuration.

Theoretical guide for clinical implementation of this technique have been developed. In conventional radiography, the primary-to-scatter ratio is improved by employing an anti-scatter grid at the cost of an increased exposure time. In phase contrast imaging with appropriate distance $R_2$ (air gap), the in-line phase-contrast method may provide scatter rejection without the need for a grid and thus lower doses might result in similar image quality.

In order to retrieve the phase information from detected signal, a theoretical formalism has been introduced for the in-line phase-contrast imaging. Normally two exposures are needed by changing the location of the image detector 40 to obtain respectively the attenuation-based image (M=1) and the phase-contrast image (M>1), from which both the amplitude and phase map of the X-ray intensity can be retrieved. Here, M is the geometrical magnification factor, defined by $$M = \frac{R_1 + R_2}{R_1}.$$

In order to reduce the dose for medical imaging systems, two detectors can be used as previously discussed, requiring only a single exposure Due to its simplicity, the in-line phase-contrast imaging method is very simple for clinical use.

Though, the DPC and in-line phase-contrast techniques are preferred solutions to be used in the stereoscopic phase-contrast imaging system of the present invention, the present invention is not limited thereto. In clear contrast, other phase-contrast X-ray imaging techniques, such as X-ray imaging by interferometer and diffraction-enhanced X-ray imaging (DEI), could alternatively be employed by the system.

With reference to FIG. 1, the imaging system 1 preferably comprises or is connectable to a stereoscopic display 70 connected to the reconstructing processor 60. This display 70 is arranged for displaying the two 2D stereoscopic phase-contrast images, preferably in a binocular stereoscopic view, in order to enable depth data interpretation. In such a stereoscopic display 70, the left eye of a viewing person preferably only sees the left-eye phase-contrast image and the right eye sees the right-eye image. In such a case, the parallax between the two images creates a strong depth perception in particular where there is a sufficient amount of high contrast structures in the images.

Figure 14:
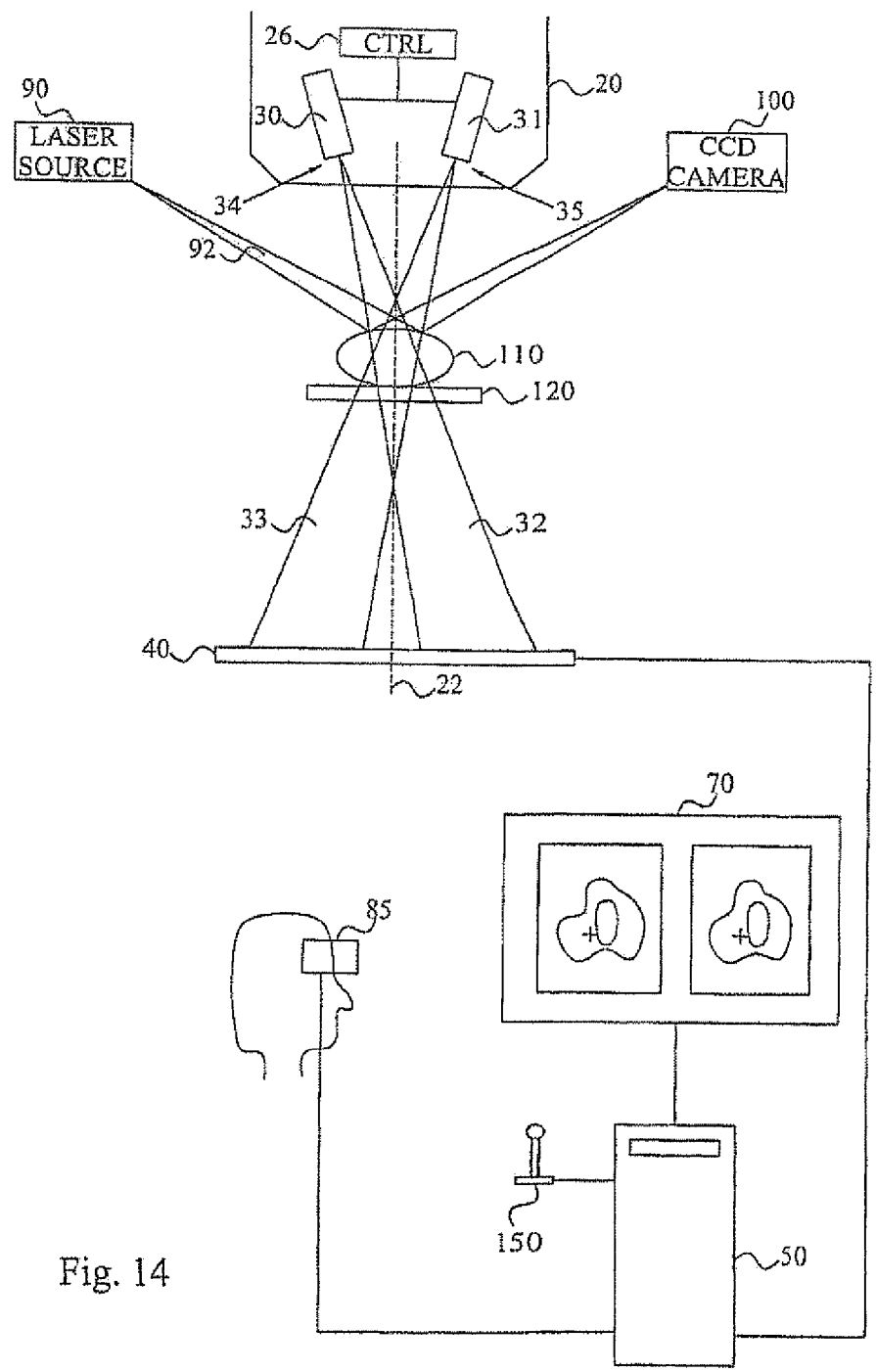
FIG. 14 is a schematic overview of a stereoscopic phase-contrast X-ray imaging system according to another embodiment of the present invention.

In order to facilitate the depth perception, stereoscopes and other tools, such as 3D eye glasses 85, see FIG. 14, can be used by the viewing persons. Such 3D eye glasses 85 include, but are not limited to, liquid crystal shutter glasses, linearly polarized glasses, circularly polarized glasses, compensating anaglyph glasses, and anachrome optical diopter glasses. However, there are 3D displays, such as displays of computers and laptops, which can be used in connection with stereoscopic images without the need of using special glasses, see for instance documents [13, 14]. Such autostereoscopic displays 70 produces a depth perception in the viewer even though the image is produced by a flat device and without the use of special headgear or glasses. Such autostereoscopic displays 70 can use lenticular lenses or parallax barrier in connection with flat-panel solutions. In such a case, the viewer will perceive a different image with each eye, giving a stereo image if he/she positions his/her head in certain viewing positions. Other displays can use eye tracking systems to automatically adjust the two displayed images to follow the viewer's eye as he/she moves his head. Such 3D displays are available from different manufactures, such as Alioscopy, Fraunhofer HHI, Holografika, i-Art, NewSight, Philips WOW VX, SeeFront, SeeReal Technologies, Spatial View, Tridelity and Sharp.

Instead of, or as a complement of having, a display 70 of a computer or laptop, a head-mounted stereoscopic display could be used. In such a case, the user wears a helmet or glasses with two small displays, such as LCD (Liquid Crystal Display) or OLED (Organic Light-Emitting Diode) displays, typically with magnifying lenses, one for each eye.

The imaging system 1 can optionally include a user input device 150 connected to the stereoscopic display 70. This user input device 150 provides a means of moving a cursor 155 over the stereo image 80, 82 on the stereoscopic display 70. This cursor 155 can be employed by the user for identifying and marking different structures (tumors), tissues and organs of interest in the images 80, 82. Such structure marking can be a highly advantageous tool in connection with collecting diagnostic information and may be used in connection with generating a treatment plan for a patient suffering from cancer.

In a preferred embodiment, the user input device 150 is a haptic user input device 155 providing a tactile depth sense to a user when moving the cursor 155 across the stereoscopic images 80, 82. This haptic device 150 provides the user with a sense of touch, such as by applying forces, vibrations and/or motions. Such tactile feedback strongly facilitates the perception of depth when moving the cursor 155 along the Z-axis of the images (Z-axis corresponds to depth, with X- and Y-axis being in the plane of the drawing). The system is preferably designed so the device cursor 155 is collocated with the 3D image of the object studies.

Toady such haptic devices 150 are available in wide range of fields from games, virtual reality to medicine and robotics from different manufactures, such as SenseGraphics AB.

When imaging an animal subject by the stereoscopic phase-contrast imaging system 1, the surface of the subject 110 may sometimes not be so well delineated in the generated stereoscopic image pair 80, 82. The reason for this is that the subject surface is rather smooth on the mm level and does not present varying attenuation or phase coefficient. In order to solve this problem, the imaging system 1 preferably comprises a surface scanning system comprising a laser scanner 90 and a photon detector 100. The laser scanner 90 and/or photon detector 100 may be connected to the gantry 10 as is illustrated in the figure but could alternatively form part of the radiation head 20, for example, mounted on the curved rail of the X-ray sources in FIG. 2 or a separate rail. It is actually possible to use stand-alone laser scanner 90 and/or detector 100 that could be arranged on dedicated racks in the wall and/or roof of the treatment room or be connected to stand-alone floor-mounted supports.

The laser scanner 90 is preferably arranged for scanning a laser fan beam 92 over at least a portion of the surface of the object 110. In such a case, the photon detector 100 is arranged for detecting the reflected laser beam 94 originating from the object surface to generate detected surface data.

The surface-scanning system could be controlled to perform a sequential surface scanning relative the phase-contrast X-ray imaging. In such a case, the surface scanning is performed prior or after the X-ray imaging. In an alternative approach, the laser scanning by the scanner 90 coincidence with the provision of the X-ray beam 32 from the X-ray source to thereby freeze or synchronize surface data to the X-ray data.

The surface-scanning system preferably provides information of the object surface with mm or even sub-mm resolution and will therefore be a perfect complement and an accurate boundary-value envelope to the internal tissue structures seen by the stereoscopic phase-contrast to form a truly accurate 3D image volume of high quality. An example of such a laser scanning system that can be used according to the present invention is commercially available by C-Rad Positioning AB under the tradename SENTINEL™ [15, 16]. The laser camera 90 can also be used for auto set up of the patient before X-ray imaging for accurate positioning of the patient for example using the rotary couch 120 of FIG. 6.

The phase-contrast stereoscopic image reconstructing processor 60 is then connected to both the at least one X-ray detector 40 and the photon detector 100. The processor 60 is therefore preferably arranged for co-processing the stereoscopic pair of detected data from the X-ray detector(s) 40 with the detected surface data from the photon detector 100. This co-processing involves generating a stereoscopic pair of 2D phase-contrast images comprising object surface structures obtained from the laser scanning system. Thus, diagnostic data from two imaging modalities, i.e. the stereoscopic phase-contrast X-ray technique and the surface laser scanning technique, are co-processed to be able to generate a (3D) stereo image that depicts diagnostic data collected by respective imaging modality.

The laser scanning system provides a significant contribution to the imaging system 1 of the present invention by being able to capture those structures, i.e. skin and subject surface, which are hardest to represent with the phase-contrast X-ray imaging. The two system therefore not only complements each other but indeed goes beyond that by being able to provide a fully 3D interpretation of vastly varying structures in an animal body, including skin and surface structures to internal tissue, organs and other structures.

FIG. 9 is a schematic block diagram of the computer or processing terminal 50 of FIG. 1 comprising the phase-contrast stereoscopic image reconstructing processor 60 of the present invention 60. The processing terminal 50 comprises a general input and output (I/O) unit 52 providing an interface between internal units and external equipment. This I/O unit 52 is in particular arranged for receiving detected X-ray data from the at least one X-ray detector of the imaging system. The I/O unit 52 preferably also receives detected surface data from the photon detector of the surface scanning system part of the imaging system. If a user input device, such as haptic device, is employed by the imaging system, user input data from the device is forwarded to the I/O unit 52. The I/O unit 52 also outputs data including the generated stereoscopic image data from the image processor 60. This data can be forwarded to a stereoscopic display, optionally a head-mounted display. Correspondingly, output control data from a haptic input controller 56 can be forwarded by the I/O unit 52 to the display to there cause a movement of a cursor over the stereo image based on the output control data.

The image processor 60 can comprises an in-line phase contrast processor 62 processing the X-ray data from the I/O unit 52 according to an in-line phase-contrast processing algorithm to generate the two stereoscopic phase-contrast images. Such in-line phase-contrast processing is well known in the art, such as disclosed by the documents [17-23] and is therefore not discussed in more detail herein.

Alternatively, or in addition, the stereoscopic image reconstructing processor comprises a DPC processor 64 for processing the X-ray data from the I/O unit 52 according to a DPC processing algorithm to generate the phase-contrast images. DPC processing is known in the art, such as illustrated by documents [24-29] and is not discussed further herein.

The stereoscopic image processor 60 also preferably uses surface data from the surface scanning system as previously discussed for the purpose of co-processing X-ray data and surface data. In either case, the generated stereoscopic image data can be forwarded directly to the I/O unit 52 for further forwarding to an external device, such as display, external data processor or external data storage. Alternatively, or in addition, the generated image data can be stored internally in a data storage 54 connected to the processor 60. In such a case, the stored data can later be retrieved and sent to the I/O unit 52 for further forwarding.

The optional haptic input controller 56 receives, via the I/O unit 52, input data from the haptic device as the user employs the device. The controller 56 preferably processes the input data for the purpose of generating cursor control data and for generating tactile feedback data. The cursor control data is sent to the stereoscopic display causing a movement of a displayed cursor or some other pointer over the image data. The feedback data is forwarded to the haptic device to provide tactile feedback to the user to thereby provide a tactile depth perception synchronized with the movement of the cursor.

The unit 52, 56, 60, 62, 64 of the processing terminal 50 may be provided as hardware, software or a combination of hardware and software. The units 52, 54, 56, 60, 62, 64 may all be implemented in the processing terminal 50. Alternatively, a distributed implementation over multiple inter-connecting terminals is also possible and within the scope of the invention.

FIG. 14 is another overview of a stereoscopic phase-contrast X-ray system according to the present invention. The figure illustrates the usage of two X-ray sources 30, 31 together with a detector 40 for generating a stereoscopic pair of phase-contrast images of an object 110. A scanning laser fan beam 92 from a laser source 90 provides, together with a dedicated CCD camera 100, a representation of the surface of the object. In the figure, a phase-contrast image display 70 is illustrated. The figure also illustrates a user equipped with a head-mounted stereoscopic display 85. The system can also include an expert system either constituting a part of the general image processing system 50 as illustrated in the figure, or be a separate entity connected to such a processing system or terminal. Such an expert system provides diagnostics and 3D/4D image processing. Finally a colocalized haptic interface 150 can be employed for target volume definition as previously described.

Figure 10:
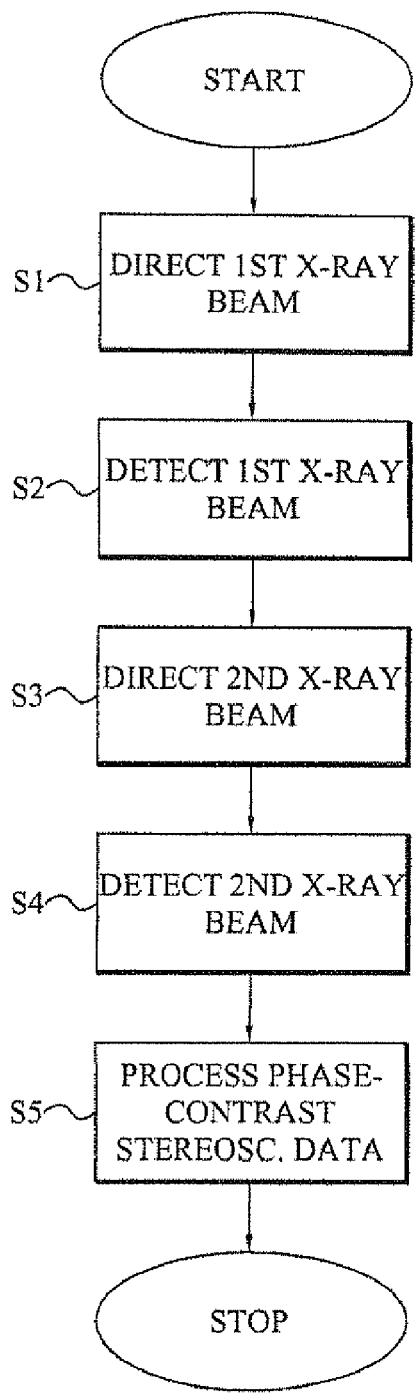
FIG. 10 is a flow diagram illustrating an embodiment of a stereoscopic phase-contrast X-ray imaging method.

FIG. 10 is a flow diagram illustrating a stereoscopic phase-contrast X-ray imaging method according to the present invention. The method starts in step S1, which involves directing a first X-ray beam onto an object positioned on a couch from a first stereoscopic radiating position. The first X-ray beam is detected in step S2 after it has passed through at least a portion of the object. The detected radiation is transformed by the at least one detector into first detected data representative of the detected X-ray radiation.

A next step S3 directs a second X-ray beam onto the object from a second stereoscopic radiating position, where the first and second positions being in stereoscopic configuration. Step S4 detects the second X-ray beam having passed through the object and generates second detected data representative of the detected X-ray radiation. The first and second detected X-ray data collectively form a stereoscopic pair of detected data.

The application and detection of the second X-ray beam in steps S3 and S4 can be performed sequentially relative to the application and detection of the first X-ray beam in steps S1 and S2 as illustrated in the figure. Alternatively, the steps S3 and S4 are performed substantially in parallel with steps S1 and S2. In such a case, directing the second X-ray beam onto the subject of step S3 coincides in time with the step S1 of directing the first X-ray beam onto the subject.

Step S5 performs a stereoscopic phase-contrast image processing of the detected data from steps S2 and S4 to generate two 2D phase-contrast images of at least a portion of the object. These two images collectively form a stereoscopic image pair or stereo image.

The processing of step S5 optionally involves co-processing the two 2D images to generate a 3D digital data set that can be displayed to a user. This co-processing can involve arranging the respective images in relative left-eye and right-eye position on a stereoscopic display.

The image processing of step S5 can involve processing the stereoscopic pair of detected data according to an in-line phase-contrast or a DPC processing algorithm as previously discussed to generate the stereoscopic image data.

FIG. 11 is a flow diagram illustrating an additional step of the imaging method of FIG. 10. The method continues from step S2 of FIG. 10. A next step S10 involves translating or moving the X-ray source from the first stereoscopic radiating position in a radiation head of the imaging system to the second radiating position. The method then continues to step S3 of FIG. 1.

In an alternative embodiment, the radiation head and optionally a movable gantry part of the imaging system is rotated relative a stationary gantry part to move the X-ray source from the first to the second stereoscopic radiating position.

FIG. 12 is a flow diagram illustrating additional steps of the imaging method of FIG. 10. The method continues from step S5 of FIG. 10. A next step S20 displays the stereoscopic images in a binocular stereoscopic view on a stereoscopic or 3D display, including such a head-mounted display. Due to the stereoscopy of the images and the stereoscopic configuration of the radiating positions, depth perception is mediated to a viewer of the stereo image.

A next optional step S21 provides haptic user feedback to a user-input device controlling a cursor or pointer movable over the stereoscopic images on the display. This haptic feedback provides a tactile depth perception that enhances the visual depth perception of the stereoscopic images. The method then ends.

Figure 13:
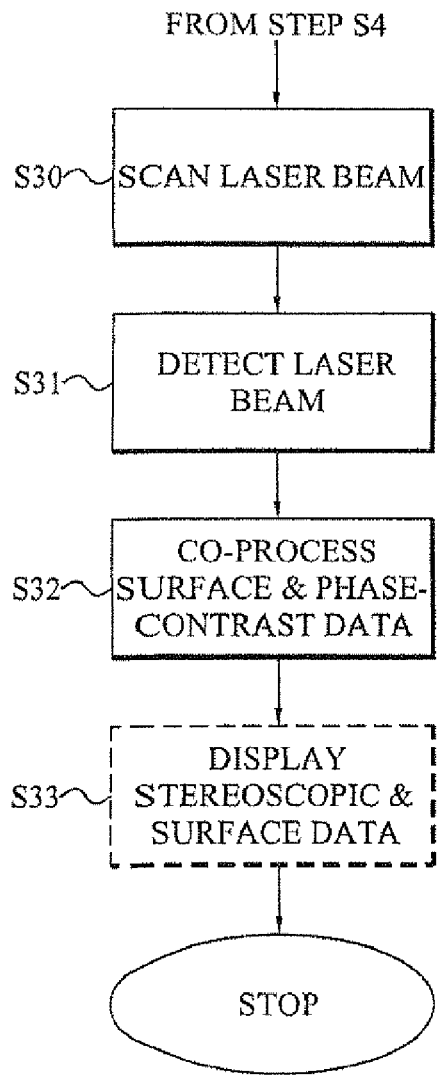
FIG. 13 is a flow diagram illustrating additional steps of the imaging method in FIG. 10.

FIG. 13 is a flow diagram illustrating an embodiment of the data processing step S5 of FIG. 10. The method continues from step S4 of FIG. 10. A next step S30 scans a laser beam, preferably laser fan beam, onto a least a portion of a surface of the object. This surface portion preferably comprises at least the surface positioned above the volume that is being imaged by the phase-contrast X-ray system.

The reflected laser beam originating from the surface portion is detected in step S31 and processed to generate surface data representative of the reflected laser beam. A next step S32 co-processes the surface and phase-contrast X-ray data to thereby generate two 2D stereoscopic images containing structural features detected by the phase-contrast X-ray imaging and surface features detected by the laser scanning. The generated images may be displayed in binocular stereoscopic view on a display to present both internal object structure but also surface structures to the viewer in 3D. The method then ends.

As has been briefly mentioned in the foregoing, the stereoscopic phase-contrast X-ray imaging system of the present invention can be used for vastly varying diagnostic and imaging purposes. The system is in particularly adapted for visualizing internal structures, tissues and organs in animal and human bodies for diagnostic and therapeutic usage.

For instance, the present invention can be used for phase-contrast X-ray angiography. X-ray angiography is an important medical imaging technique to visualize blood vessels and their associated structures. For example, coronary artery angiography is an important clinical technique, which provides detailed high-resolution images of the vascular tree of the heart. In conventional coronary angiography, a catheter is inserted into the iliac artery and guided through the aorta and to the beginning of coronary arteries. An iodine-containing contrast agent is injected into the artery and radiographs are then taken at short intervals. If the stenosis is not too severe, the coronary angiography is followed by balloon-tipped angioplasty. The method is well developed, but still complications and even mortality are too frequent to allow conventional coronary angiography to be used as a routine diagnostic method for screening or follow-up studies. Attempts to avoid the risks by intravenous injection of the contrast agent may however fail since, by the time the bolus reaches the coronary arteries, it is usually diluted to a few percent of the initial concentration. The use of heavy element contrast agents may also cause allergic reactions and vascular damage in some patients.

Stereoscopic phase-contrast X-ray imaging techniques are well suited for angiography applications without the problems of traditional coronary angiography. It turns out that this new X-ray imaging technique may offer improved opportunities in angiography due to its excellent contrast for soft tissue imaging. Although, for some vascular systems of clinical interest, contrast agents may still be required also for phase-contrast X-ray imaging, new types of contrast agents without heavy elements may be introduced to reduce some of the negative effects. For instance, physiological saline could be used as a contrast agent instead of iodine and other heavy elements.

It is expected that with the present invention, it is possible to image blood vessels in thick objects of soft tissues. If a sufficiently high-flux-density X-ray beam is available, it is also possible to make dynamic phase-contrast X-ray imaging of blood flow conditions in blood vessel structures of clinical interest, such as those in tumors since a hypoxic tumor stimulates the creation of new blood vessels for improved oxygen and nutritional supply. Here, in comparison with other imaging modalities, the stereoscopic phase-contrast X-ray imaging method may offer extremely high-resolution images that are required to visualize blood capillaries. Such a study could also be potentially useful for investigating blood flow conditions helpful in understanding drug delivery mechanisms among others. At present, X-ray beams with extremely high flux density are in particular available at large synchrotron radiation-based X-ray facilities, which can be used in the present imaging system.

Another potential use of the imaging system is in connection with cartilage bone and cancellous bone imaging. Non-invasively detection of cartilage abnormalities is important to discover initial stages and early progression of degenerative joint disease or osteoarthritis. At present, osteoarthritis is a prevalent and poorly understood disease that affects the cartilage and other tissues in the joints of aging people, having a serious impact on the quality of life. Information on the structure of normal cartilage and the ways in which this tissue, with limited or no ability to repair, changes after damage or disease is essential for the development of rational treatment strategies. However, conventional attenuation-based contrast radiology is sensitive only in the case of advanced disease in which there has been a loss of cartilage. Other alternative imaging methods, such as magnetic resonance imaging and ultrasound, have generally poorer spatial resolution than X-rays.

With the use of the stereoscopic phase-contrast X-ray imaging of the invention, it is now possible to visualize cartilage and detect early degenerative changes. For instance, by using the DEI X-ray imaging technique with a synchrotron radiation source, human articular cartilage is not only visible, but also gross cartilage defects, even at early stages of development, can be visualized due to the combination of high spatial resolution and detection of X-ray refraction, extinction and absorption patterns in the DEI images.

The DEI technique and other phase-contrast imaging techniques is also capable of rendering high-contrast images of bone and can be used to visualize the edges of cortical and cancellous bone. The refractive properties of spongy or cancellous bone architecture may then provide a 3D architectural appearance: a feature that is lost in conventional radiography.

The present system is particularly suitable for thorax imaging, such as lung, breast and/or heart imaging. Conventional attenuation-based radiography has hade limited-success in detecting lung diseases, in which the variation in tissue density created by a pathological process is often too small to be detected, especially for early stage lung diseases. Even in their more advanced stages some diseases, particularly interstitial lung disease can show completely normal (healthy) chest radiographs. A significant degree of X-ray phase contrast is created at the air-tissue interfaces in lung and makes it an ideal candidate for diagnostic improvement using phase contrast X-ray imaging techniques. With the phase-contrast, the lung tissue clearly stands out from surrounding soft tissues. Here, the improved visibility of the lung results from the speckled intensity pattern.

Nowadays, breast cancer is one of the dominating causes of death of women in industrialized countries. Although very early detection of breast cancer may lead to almost 100% successful therapy, practical use of mammography for systematic screening of breast cancer has so far been quite limited due to the weak attenuation-contrast of conventional X-ray imaging techniques in differentiating soft tissues, especially normal and abnormal breast tissues at small scales, where the elemental composition is almost uniform and the density variations are small. However, the phase-contrast imaging techniques of the invention could visualize microstructures of soft biological tissues under low radiation dose.

Since microcalcifications of about 100 μm are the most critical objects in the breast tissue that may provide an indication for breast cancer, a high spatial resolution with the mammography system is therefore mandatory. Due to the dramatic contrast enhancement and resolution increase by stereoscopic phase-contrast X-ray imaging, the use of digital detectors of high quantum efficiency may provide a dose reduction factor of 5-10.

By taking into account multiple contrast mechanisms (absorption, refraction, scattering), stereoscopic phase-contrast X-ray imaging may lead to further improvements in system performance in multi-contrast mammography.

Like conventional radiography, phase-contrast X-ray imaging techniques offer projected 2D images on which tissue structures can be visualized. However, since the projection of 3D anatomic information onto a 2D image will obscure subtle differences in X-ray transmission, the subtle difference in subject attenuation-contrast may not be visible in conventional X-ray images. This will also be the case for phase-contrast X-ray imaging. This difficulty can largely be eliminated by the stereoscopic phase-contrast X-ray imaging allowing the full 3D or 4D (3D+time) anatomy to be appreciated in one or multiple stereo images. Its superior visualization of subject contrast, together with depth localization and display of anatomy across planes that are not accessible by conventional imaging techniques will make the stereoscopic phase-contrast imaging exceptionally useful for visualizing anatomy in the living body.

The large amount of extra information in a projected phase-contrast image will, as has been mentioned, make it very difficult to interpret a single projected image of a thick complex object. However, by always registering a stereoscopic pair of images, the different phase contrast signatures can not only be separated in their x and y axis projections but also along a depth axis z, using a stereoscopic readout system. With ordinary attenuation contrast, stereoscopic imaging was never very popular since the contrast was too weak and it was difficult to get a good 3D impression as the structures to form the 3D image contained very little information. This situation is reversed with phase-contrast imaging since the high amount of image information and structure can now be used to significantly improve the 3D visibility of thick phase contrast objects simply by stereoscopic imaging. So even if each projected image of a stereoscopic pair is hard to interpret on its own, the high amount of phase contrast objects makes them clearly distinguishable in 3D stereoscopic view. This opens up the field of 3D phase contrast imaging to low dose imaging with only two planar projections instead of more than 300 images needed for good computed tomography reconstruction. Obviously the exposure time for each of the CT projections need not to be as long as for each of the images of the stereoscopic pair. However, there may still be a substantial saving in patient exposure at the same time as it is not necessary to rotate the X-ray source around the patient. The stereoscopic phase contrast technique is therefore suitable for use with many of the new generation of difficult to rotate but advanced X-ray sources, such as synchrotrons, wigglers, monochromators, free-electron lasers and liquid metal jet targets. Not only can the stereoscopic pair be generated by only a small rotation of the object or beam and detector or using two separate imaging channels, but it will also reduce the exposure significantly, including substantial reduction of the imaging time.

With the use of two simultaneous imaging channels, it will even be possible to do instantaneous imaging, freezing organ motion down to milliseconds and even faster. This can be especially desirable in the thorax region with heartbeat and breathing motions that otherwise may blur and even remove a substantial part of the new phase contrast information.

Thus, the present system and method can advantageously be used for tumor imaging and cancer diagnostic, including imaging of, for example, thorax (breast, lung, heart), head, neck and brain tumors.

Due to its high contrast and resolution, the system can also be used for other diagnostic purposes such as in drug delivery mechanisms in novel target-specific nano-drug delivery systems for treating cancers.

Though the present invention is highly suitable for imaging of biological objects, the imaging system can also be employed for non-biological imaging.

An example of the latter is security control imaging, product inspection and analysis of non-metallic materials.

All the references cited herein and listed under the reference section are hereby fully incorporated by references and regarded as constituting a portion of the present description.

It will be understood by a person skilled in the art that various modifications and changes may be made to the present invention without departure from the scope thereof, which is defined by the appended claims.

REFERENCES

[1] Petroff, "The future of synchrotron radiation", *J Electron Spectrosc Relat Phenom*, 2007, 156-158:10-19
[2] Hemberg et al., "Liquid-metal-jet anode electron-impact X-ray source", *Appl Phys Lett*, 2003, 83:1483-1485
[3] Carroll et al., "Production of tunable, monochromatic X-rays by the Vanderbilt free-electron laser", *Proc SPIE, Free Electron Laser Challenges II*, 1999, 3614:139-146
[4] Uesaka et al., "Monochromatic tunable Compton scattering X-ray source using X-band multi-bunch linac and YAG laser circulation system", *Nucl Instrum Methods Phys Res*, 2007, B261:867-870
[5] Yamada, "Novel X-ray source based on a tabletop synchrontron and its unique features", *Nucl Instrum Meth Phys Res*, 2003, B199:509-516
[6] Yorkston, "Recent developments in digital radiography detectors", *Nucl Instrum Meth Phys Res*, 2007, A580:974-985
[7] Darambara, "State-of-the-art radiation detectors for medical imaging: demands and trends", *Nucl Instrum Meth Phys Res*, 2007, A569:153-158
[8] Sarvestani et al., "Microsecond time-resolved 2D X-ray imaging", *Nucl Instrum Meth Phys Res*, 2001, A465:354-364
[9] Östling, "New efficient detector for radiation therapy imaging using gas electron multipliers", *Ph.D. thesis* 2006, Karolinska Institutet and Stockholm University, Dept Med Rad Phys
[10] U.S. Pat. No. 6,891,166
[11] U.S. Pat. No. 6,841,784
[12] US Patent Application No. 2007/0274435
[13] Hill et al., "3-D liquid crystal displays and their applications", *Proc IEEE*, 2006, 94(3):575-590
[14] Dodgson, "Autostereoscopic 3D displays", *Computer*, 2005, 38(8):31-36
[15] Brahme et al., "4D Laser Camera for accurate patient positioning, collision avoidance, image fusion and adaptive approaches during diagnostic and therapeutic procedures", *Med Phys*, 2008 (in press)
[16] International Application No. WO 2004/000120
[17] Snigirev et al., "On the possibilities of X-ray phase contrast microimaging by coherent high-energy synchrotron radiation", *Rev Sci Instrum*, 1995, 66:5486-5492
[18] Wilkins et al., "Phase-contrast imaging using polychromatic hard X-rays", *Nature*, 1996, 384:335-338
[19] Wu et al., "Clinical implementation of X-ray phase-contrast imaging: theoretical foundations and design considerations", *Med Phys*, 2003, 30(8):2169-2179
[20] Wu et al., "Optimization of X-ray phase-contrast imaging based on in-line holography", *Nucl Instrum methods Phys Res*, 2005, B234:563-572
[21] Wu et al., "A general theoretical formalism for X-ray phase contrast imaging", *JX-ray Sci Technol*, 2003, 11(1):33
[22] Meng et al., "An iterative phase retrieval algorithm for in-line x-ray phase imaging", *Opt Expr*, 2007, 15(13):8383-8390
[23] Meng et al., "Development of a dual-detector X-ray imaging system for phase retrieval study" *Nucl Instrum Methods Phys Res*, 2007, B254:300-306
[24] David C, Nohammer B, Solak H H, Ziegler E. Differential x-ray phase contrast imaging using a shearing interferometer. Appl Phys Lett 2002; 81:3287-3289.
[25] Momose et al., "Demonstration of X-ray Talbot interferometry", *Jpn J Appl Phys*, 2003, 42(7B):L866-L868
[26] Pfeiffer et al., "Phase retrieval and differential phase-contrast imaging with low-brilliance X-ray sources", *Nat Phys*, 2006, 2:258-261
[27] David et al., "Fabrication of diffraction gratings for hard X-ray phase contrast imaging", *Microeng Eng*, 2007, 84:1172-1177
[28] Talbot, "Facts relating to optical science", *No. IV Philos Mag*, 1836, 9:401-407
[29] Weitkamp et al., "Quantitative X-ray phase imaging with a grating interferometer", *Opt Expr*, 2005, 13:6296-6304

The invention claimed is:

1. A phase-contrast X-ray imaging system comprising:
a stereoscopic X-ray radiation head comprising at least one X-ray source arranged for directing a first X-ray beam and a second X-ray beam in stereoscopic configuration onto an object;
at least one X-ray detector arranged for detecting said first X-ray beam and said second X-ray beam having passed through said object to generate a stereoscopic pair of detected data;
a laser scanner arranged for scanning a laser fan beam onto at least a portion of a surface of said object;
a photon detector arranged for detecting a reflected laser beam originating from said at least a portion of said object surface to generate detected surface data; and
a phase-contrast stereoscopic image reconstructing processor connected to said at least one X-ray detector and said photon detector and arranged for co-processing said stereoscopic pair of detected data and said detected surface data to generate a 3D data set limited by said surface data and comprising two two dimensional phase-contrast images of at least a portion of said object collectively fanning a stereoscopic image pair.

2. A phase-contrast X-ray imaging system comprising:
a stereoscopic X-ray radiation head comprising at least one X-ray source arranged for directing a first X-ray beam and a second X-ray beam in stereoscopic configuration onto an object;
at least one X-ray detector arranged for detecting said first X-ray beam and said second X-ray beam having passed through said object to generate a stereoscopic pair of detected data; and
a phase-contrast stereoscopic image reconstructing processor connected to said at least one X-ray detector and arranged for processing said stereoscopic pair of detected data to generate two two-dimensional phase-contrast images of at least a portion of said object collectively forming a stereoscopic image pair.

3. The system according to claim 2, Wherein said stereoscopic X-ray radiation head comprises a source translator arranged for translating said X-ray source from a first stereoscopic radiating position directing said first X-ray beam onto said object to a second stereoscopic radiating position directing said second X-ray beam onto said object.

4. The system according to claim 2, wherein said stereoscopic X-ray radiation head comprising:
   a first X-ray source positioned in a first stereoscopic radiating position and arranged for directing said first X-ray beam onto said object; and
   a second X-ray source positioned in a second stereoscopic radiating position and arranged for directing said second X-ray beam onto said object.

5. The system according to claim 4, further comprising a source controller connected to said first X-ray source and said second X-ray source and arranged for controlling the timing of directing said first X-ray beam by said first X-ray source to coincide in time with the timing of directing said second X-ray beam by said Second X-ray Source.

6. The system according to claim 4, wherein said first and second stereoscopic radiating positions are positioned to the left respective to the right of a central axis of the imaging system in a plane parallel to an imaging plane.

7. The system according to claim 2, wherein said at least one X-ray source is arranged for directing said first X-ray beam and said second X-ray beam with a beam pulse duration of no lucre than 1 μs.

8. The system according to claim 2, wherein said at least one X-ray source is a microfocus X-ray source.

9. The system according to claim 2, wherein said at least one X-ray source is selected from the groups consisting of a synchrotron X-ray source, a free electron laser X-ray source, an inverse Compton X-ray source, a laser-driven X-ray source and a liquid-metal-jet X-ray source.

10. The system according to claim 2, further comprising:
    a first X-ray detector arranged for detecting said first X-ray beam having passed through said object to generate first detected data; and
    a second X-ray detector arranged for detecting said second X-ray beam having passed through said object to generate second detected data, said first and second detected data collectively form said stereoscopic pair of detected data.

11. The system according to claim 2, wherein said at least one X-ray detector is at least one two-dimensional gas electron multiplier X-ray detector.

12. The system according to claim 2, wherein said phase-contrast stereoscopic image reconstructing processor comprises an in-line phase-contrast processor arranged for processing said stereoscopic pair of detected data according to an in-line phase-contrast processing algorithm to generate said two two-dimensional phase-contrast images of said at least a portion of said object collectively forming a stereoscopic image pair.

13. The system according to claim 2, further comprising a Talbot X-ray interferometer arranged between said object and said at least one X-ray detector.

14. The system according to claim 2, wherein said phase-contrast stereoscopic image reconstructing processor comprises a differential phase-contrast processor arranged for processing said stereoscopic pair of detected data according to a differential phase-contrast processing algorithm to generate said two two-dimensional phase-contrast images of said at least a portion of said object collectively forming a stereoscopic image pair.

15. The system according to claim 2, further comprising a stereoscopic display connected to said stereoscopic image reconstructing processor and arranged for displaying said two two-dimensional phase-contrast images in a binocular stereoscopic view.

16. The system according to claim 15, further comprising a haptic user-input device connected to said stereoscopic display and arranged for providing a tactile depth sense of a cursor movable over said two two-dimensional phase-contrast images on said stereoscopic display.

17. A phase-contrast X-ray imaging method comprising:
    directing a first X-ray beam onto an object from a first stereoscopic radiating position;
    detecting said first X-ray beam having passed through said object to generate first detected data;
    directing a second X-ray beam onto said object from a second stereoscopic radiating position, said first and second radiating positions being in stereoscopic configuration;
    detecting said second X-ray beam having passed through said object to generate a second detected data, said first and second detected data collectively forming a stereoscopic pair of detected data;
    scanning a laser fan beam onto at least a portion of a surface of said object;
    detecting a reflected laser beam originating from said at least a portion of said object surface to generate detected surface data; and
    phase-contrast stereoscopic image co-processing said stereoscopic pair of detected data and said detected surface data to generate a 3D data set limited by said surface data and comprising two two-dimensional phase-contrast images of at least a portion of said object collectively forming a stereoscopic image pair.

18. A phase-contrast X-ray imaging method comprising:
    directing a first X-ray beam onto an object from a first stereoscopic radiating position;
    detecting said first X-ray beams having passed through said object to generate first detected data;
    directing a second X-ray beam onto said object from a second stereoscopic radiating position, said first and second radiating positions being in stereoscopic configuration;
    detecting said second X-ray beam having passed through said object to generate a second detected data, said first and second detected data collectively forming a stereoscopic pr of detected data; and
    phase-contrast stereoscopic image processing said stereoscopic pair of detected data to generate two two-dimensional phase-contrast images of at least a portion of said object collectively forming a stereoscopic image pair.

19. The method according to claim 18, wherein said processing step comprises stereoscopically co-processing said two two-dimensional phase-contrast images to generate a three-dimensional digital data set.

20. The method according to claim 18, further comprising translating an X-ray source from said first stereoscopic radiating position to said second stereoscopic radiating position.

21. The method according to claim 18, wherein said step of directing said second X-ray beam onto said object coincides with said step of directing said first X-ray beam onto said object.

22. The method according to claim 18, wherein said processing step comprises processing said stereoscopic pair of detected data according to an in-line phase-contrast processing algorithm to generate said two two-dimensional phase-contrast images of said at least a portion of said object collectively forming a stereoscopic image pair.

23. The method according to claim 18, wherein said processing step comprises processing said stereoscopic pair of detected data according to a differential phase-contrast processing algorithm to generate said two two-dimensional phase-contrast images of said at least a portion of said object collectively forming a stereoscopic image pair.

24. The method according to claim 18, further comprising displaying said two two-dimensional phase-contrast images in a binocular stereoscopic view on a stereoscopic display.

25. The method according to claim 24, further comprising providing haptic, tactile depth user-feedback to a user-input device controlling a cursor movable over said two two-dimensional phase-contrast images on said stereoscopic display.

* * * * *

UNITED STATES PATENT AND TRADEMARK OFFICE
CERTIFICATE OF CORRECTION

PATENT NO. : 7,693,256 B2  Page 1 of 1
APPLICATION NO. : 12/051264
DATED : April 6, 2010
INVENTOR(S) : Anders Brahme et al.

It is certified that error appears in the above-identified patent and that said Letters Patent is hereby corrected as shown below:

In claim 5, column 21, line 22, after "said", delete "Second X-ray Source".

In claim 5, column 21, line 22, after "said", insert --second X-ray source--.

In claim 7, column 21, line 30, after "no", delete "lucre".

In claim 7, column 21, line 30, after "no", insert --more--.

Signed and Sealed this

Thirteenth Day of July, 2010

David J. Kappos
*Director of the United States Patent and Trademark Office*